(12) United States Patent
Sabins et al.

(10) Patent No.: US 6,345,535 B1
(45) Date of Patent: Feb. 12, 2002

(54) APPARATUS AND METHOD FOR ESTIMATING THE COMPRESSIVE STRENGTH OF FOAM CEMENT

(75) Inventors: Fred L. Sabins, Sugar Land; Voldi E. Maki, Jr., Austin, both of TX (US)

(73) Assignee: Chandler Engineering Company LLC, Broken Arrow, OK (US)

( * ) Notice: Subject to any disclaimer, the term of this patent is extended or adjusted under 35 U.S.C. 154(b) by 0 days.

(21) Appl. No.: 09/596,299

(22) Filed: Jun. 17, 2000

(51) Int. Cl.[7] ................................................ G01N 3/00
(52) U.S. Cl. ...................................................... 73/818
(58) Field of Search ........................... 73/818, 822, 823, 73/19.08, 862.392, 862.391, 824

(56) References Cited

U.S. PATENT DOCUMENTS

| | | | |
|---|---|---|---|
| 4,259,868 A | | 4/1981 | Rao et al. |
| 4,567,765 A | | 2/1986 | Rao et al. |
| 5,846,462 A | * | 12/1998 | Thompson .................... 264/51 |
| 5,853,475 A | * | 12/1998 | Liskowitz et al. .......... 106/705 |
| 5,992,223 A | | 11/1999 | Sabins et al. |

* cited by examiner

*Primary Examiner*—Benjamin R. Fuller
*Assistant Examiner*—Andre Allen
(74) *Attorney, Agent, or Firm*—Fellers, Snider, Blankenship, Bailey & Tippens, P.C.

(57) ABSTRACT

A method of estimating the compressive strength of a foam cement sample from a parametric measurement (base cement compressive strength) obtainable from conventional equipment, wherein standard laboratory measurements are used to establish the relationship between the base cement compressive strength, the volume percent entrained gas and the compressive strength of the subject foam cement.

13 Claims, 3 Drawing Sheets

APPARATUS AND METHOD FOR ESTIMATING THE COMPRESSIVE STRENGTH OF FOAM CEMENT

BACKGROUND OF THE INVENTION

1. Field of the Invention

This invention relates generally to a method and system for testing oil well cement samples, and, more specifically, to estimating the compressive strength of a foam cement sample.

2. Background

It is important to know the properties of a cement formulation to ensure its acceptability for a given application, and to be meaningful, tests must simulate actual job conditions. For numerous reasons, the compressive strength of cement used in oil field applications must be known.

Historically, in order to determine the compressive strength of cement as a function of time a multiplicity of samples of the cement have been prepared in small test cylinders, or cubes. The samples are subsequently crushed as a function of time as the cement cures. In testing batches of cement in this manner, while the cement may be cured at elevated temperatures and pressures such as are present in a wellborn environment, it is necessary to remove the cement samples from the heated pressure vessel in order to perform the crush test on the strength measuring machines required for this purpose. Thus the actual testing of cement samples is performed usually at room temperature and at atmospheric pressure. Such mechanical testing is inconvenient, cumbersome and time consuming and may in some circumstances be of questionable accuracy.

While crush tests on hardened cement samples may be used to mechanically determine the compressive strength of a cement formulation, a more recent method involves subjecting a cement or cement slurry sample to simulated oil field temperatures and pressures, measuring the transit time of an acoustic signal transmitted through the sample, and correlating the transit time to compressive strength using empirically developed equations. Compressive strength measurements using this method are often taken in what is known as the Ultrasonic Cement Analyzer (UCA). The UCA generally consists of a high temperature-high pressure autoclave, a heat jacket capable of heating rates up to 5.6° C. (10° F.) per minute, a pair of ultrasonic transducers (preferably but not necessarily operating at a frequency of about 400 kHz) for measuring the transit time of an acoustic signal transmitted through the slurry, plus associated hydraulic plumbing. The two transducers make transit time measurements through the cement as it sets. A short pulse on a lower transducer propagates through the cement to an upper transducer. Set time and compressive strength are calculated from measured transit time via empirically developed equations. U.S. Pat. Nos. 4,259,868 and 4,567,765 disclose the UCA in detail and are incorporated herein by reference.

Current practices in oilfield cementing technology provide for the introduction of various amounts of gas in cement to produce foam cement. Foam cements have been developed for oilfield applications to solve problems associated with weak formations and fluid flow problems, particularly in deep water applications. Presently, in areas where weak zones will support only a limited height of normal-density cement without breaking down, stage tools or other techniques are used to obtain the required cement sheath without producing a hydrostatic pressure that will fracture the formation. These techniques require multiple applications of cement, which is very expensive. The development of foam cements allows production of cements having densities as low as 8.0 ppg rather than the typical 12.5 ppg of a light weight non-foam cement.

It remains important, though, to know the compressive strength of a foam cement. Unfortunately, excessive attenuation of the acoustic signal through the foam cement sample often renders the typical measurement method useless. Moreover, even if an adequate signal were available for measurement, generating and maintaining a foam cement in a vessel at high pressure is problematic and requires expensive equipment.

It may thus be appreciated that there exists a need for a manner of nondestructively testing a foam cement or foam cement slurry sample to determine the compressive strength thereof.

SUMMARY OF THE INVENTION

The present inventors have discovered that foam cement compressive strength is related to the base cement compressive strength and the volume percent foam. Applying this discovery, the present invention provides a method of estimating the compressive strength of a foam cement sample from a parametric measurement (base cement compressive strength) obtainable from conventional equipment, wherein standard laboratory measurements are used to establish the relationship between the base cement compressive strength, the volume percent entrained gas and the compressive strength of the subject foam cement.

In connection with the present invention, a set of curves is preferably obtained representing the measured crush strength of foam cement samples possessing one or more volume percent entrained gas as a function of the base cement compressive strength. A mathematical surface is generated with base cement compressive strength and percent entrained gas by volume as the X and Y coordinates respectively and foam cement compressive strength as the Z-axis. The foam cement compressive strength is obtained by measuring the base cement compressive strength by any method to determine the X axis value, and, knowing the volume percent entrained gas as the Y coordinate, determining the foam cement compressive strength from the Z-axis value of the mathematical surface.

The mathematical surface also may be expressed by an equation which is accessible by a control computer of a conventional compressive strength measurement system such as the UCA. If a UCA is used to measure the base cement compressive strength, the foam cement compressive strength may be computed over time as the cement sets, so long as the volume percent entrained gas is known. In the most preferred embodiment of the invention, the method thus comprises maintaining a base cement slurry sample at controlled temperature and pressure; transmitting an ultrasonic signal through the sample; detecting the ultrasonic signal subsequent to its transiting the sample and measuring the time required for said signal to transit the sample; determining, according to a predetermined relationship relating transit time to compressive strength, the compressive strength of the sample; determining, according to a predetermined relationship relating base cement compressive strength and volume percent entrained gas to foam cement compressive strength, the compressive strength of a foam cement having a given percent entrained gas by volume; and displaying or recording the compressive strength of said foam cement.

The present invention accordingly provides an efficient and cost effective method using established laboratory techniques to obtain foam cement compressive strength at temperature and pressure as a function of time. The method is convenient and efficient insofar as it utilizes easily obtainable laboratory data measured from multiple foam cement samples to predict the foam cement compressive strength on other samples of interest based only upon the base cement compressive strength and the percent entrained gas in the desired foam cement.

A better understanding of the present invention, its several aspects, and its advantages will become apparent to those skilled in the art from the following detailed description, taken in conjunction with the attached drawings, wherein there is shown and described the preferred embodiment of the invention, simply by way of illustration of the best mode contemplated for carrying out the invention.

DETAILED DESCRIPTION OF THE PREFERRED EMBODIMENT

Before explaining the present invention in detail, it is important to understand that the invention is not limited in its application to the details of the embodiments and steps described herein. The invention is capable of other embodiments and of being practiced or carried out in a variety of ways. It is to be understood that the phraseology and terminology employed herein is for the purpose of description and not of limitation.

The ability to estimate a physical quality of a cement sample using a parametric measurement has been demonstrated. Rao and Sutton in U.S. Pat. No. 4,259,868, previously incorporated by reference, demonstrated that the compressive strength of cement may be accurately predicted using the transit time in the cement of an acoustic signal. Sabins and Maki in U.S. Pat. No. 5,992,223, hereby incorporated by reference, demonstrated that the gel strength of the cement may also be predicted using the attenuation of an acoustic signal. Each of these parametric measurements were developed using standard laboratory measurements to establish the relationship between the parametric value and the physical quality to be measured.

In the present invention, samples of cement were tested with various densities, various additives and various amounts of entrained gas. Each of the samples was made according to American Petroleum Institute procedures. The compressive strength of each sample was measured using a crush test of the sample. The cement containing no entrained gas (hereinafter referred to as the "base cement") was also measured using an Ultrasonic Cement Analyzer to confirm the accuracy of measuring the compressive strength using acoustic techniques. The acoustic technique allows for easy measurement of the time history of the development of compressive strength at typical oil well temperatures and pressures. Analysis of the data showed that the most significant factors in predicting the compressive strength of the foam cement were the compressive strength of the base, un-foamed cement and the volume per cent gas in the foam cement. Surprisingly, other factors such as the density of the base cement or the setting time of the cement were found to be less significant in the compressive strength relationship.

The inventive method accordingly preferably relates foam cement compressive strength to the factors of base cement compressive strength and volume percent entrained gas. Knowing these two factors allows for the determination, according to the predetermined relationship, of the compressive strength of a foam cement having a given percent entrained gas by volume.

The present invention will be further understood with reference to the following non-limiting experimental examples.

Figure 1:
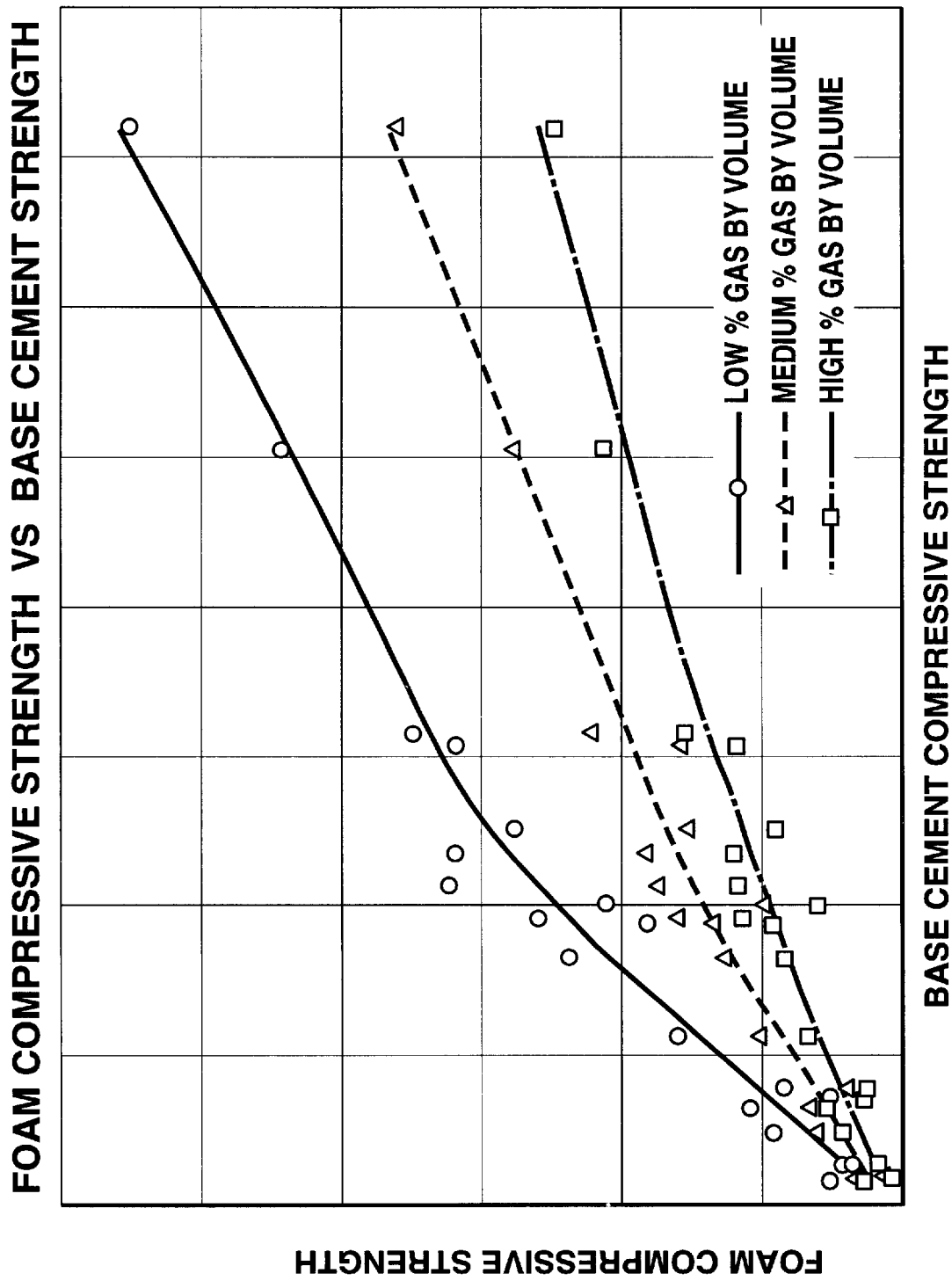
FIG. 1 is a set of curves showing the measured crush strength of foam cement samples possessing different volume percent entrained gas as a function of base cement compressive strength.

FIG. 1 is a set of curves illustrating data used to develop the relationship required to predict foam cement compressive strength. The curves show the measured crush strength of foam cement samples possessing different volume percent entrained gas as a function of base cement compressive strength. The horizontal axis is the compressive strength of the base cement, while the vertical axis is the compressive strength of the foam cement. Both values are determined from crush test data. Three different gas concentrations are shown. A best fit mathematical function, found in this case to be a 4th order polynomial, is then used to estimate the foam cement compressive strength for all values of base cement compressive strength for each value of gas concentration. More generally, it is anticipated that empirically collected data values will be fit by a function characterized by one or more constant coefficients. Further, it is preferable that a separate fit be calculated for each gas concentration, although those skilled in the art will recognize that this is not essential to the operation of the instant invention.

Figure 2:
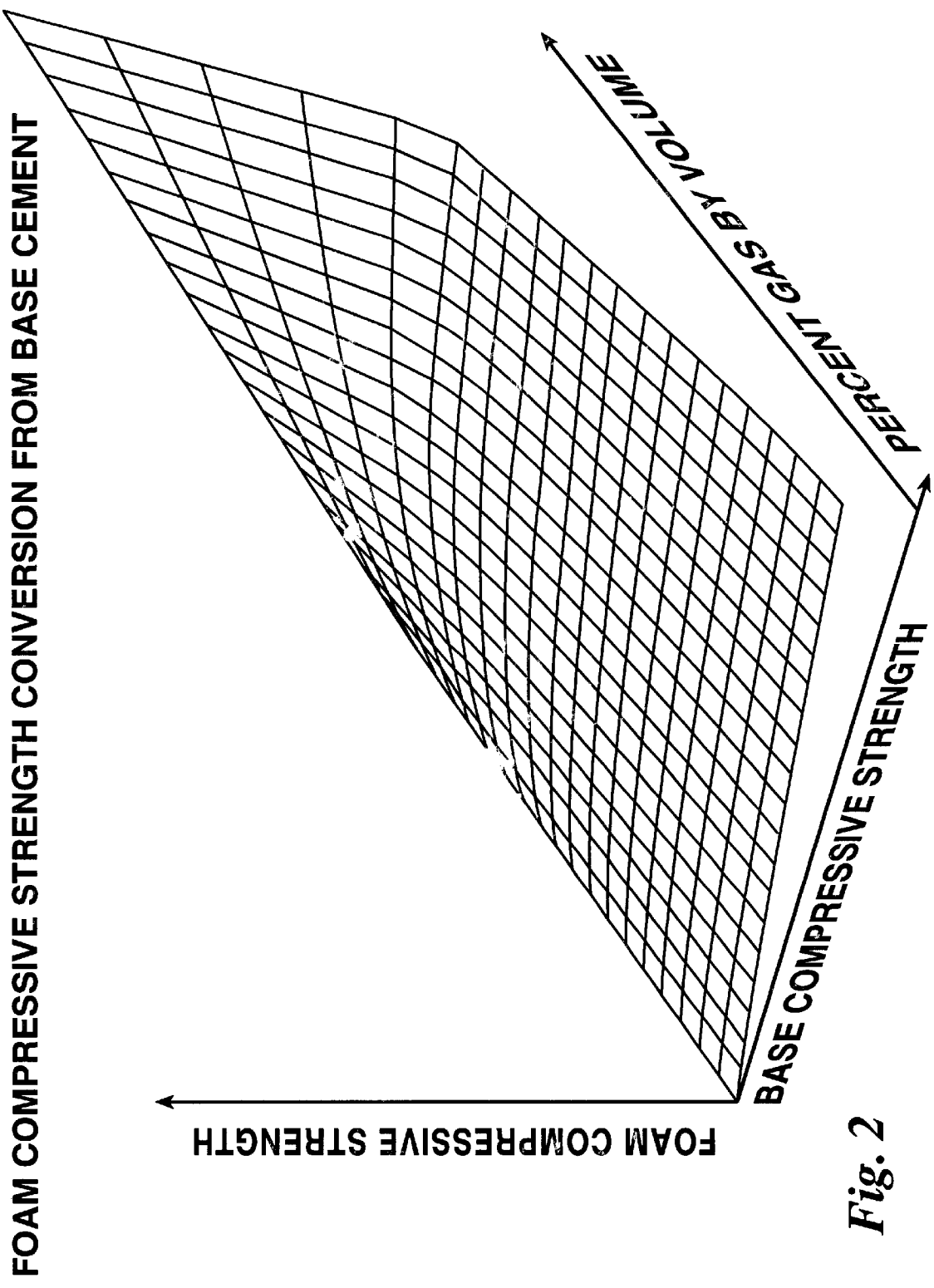
FIG. 2 shows a surface describing the conversion of the base cement compressive strength and volume percent entrained gas to foam cement compressive strength.

Linear interpolation between the calculated curves is then preferably used to generate a three-dimensional surface which is used to estimate the compressive strength at any gas concentration, with extrapolation being used where gas concentrations and compressive strengths are encountered that are outside of the bounds of those tested in the laboratory. The surface graphically describes the conversion of the base cement compressive strength and volume percent entrained gas to foam cement compressive strength. That being said, those of ordinary skill in the art will recognize that any sort of interpolation (e.g., higher or polynomials, splines, nonlinear curve fitting, etc.) might be used to generate values that are intermediate between the calculated curves. Additionally, it is certainly possible and has been specifically contemplated by the instant inventors, that the raw 3-dimensional data points might be directly fit using any curve fitting routine, those by directly generating a three dimensional surface suitable for use with the instant invention. FIG. 2 shows a mathematical surface generated in this manner, which surface provides an accurate estimate of the compressive strength of a foam cement as a function of gas concentration and base cement compressive strength.

Figure 3:
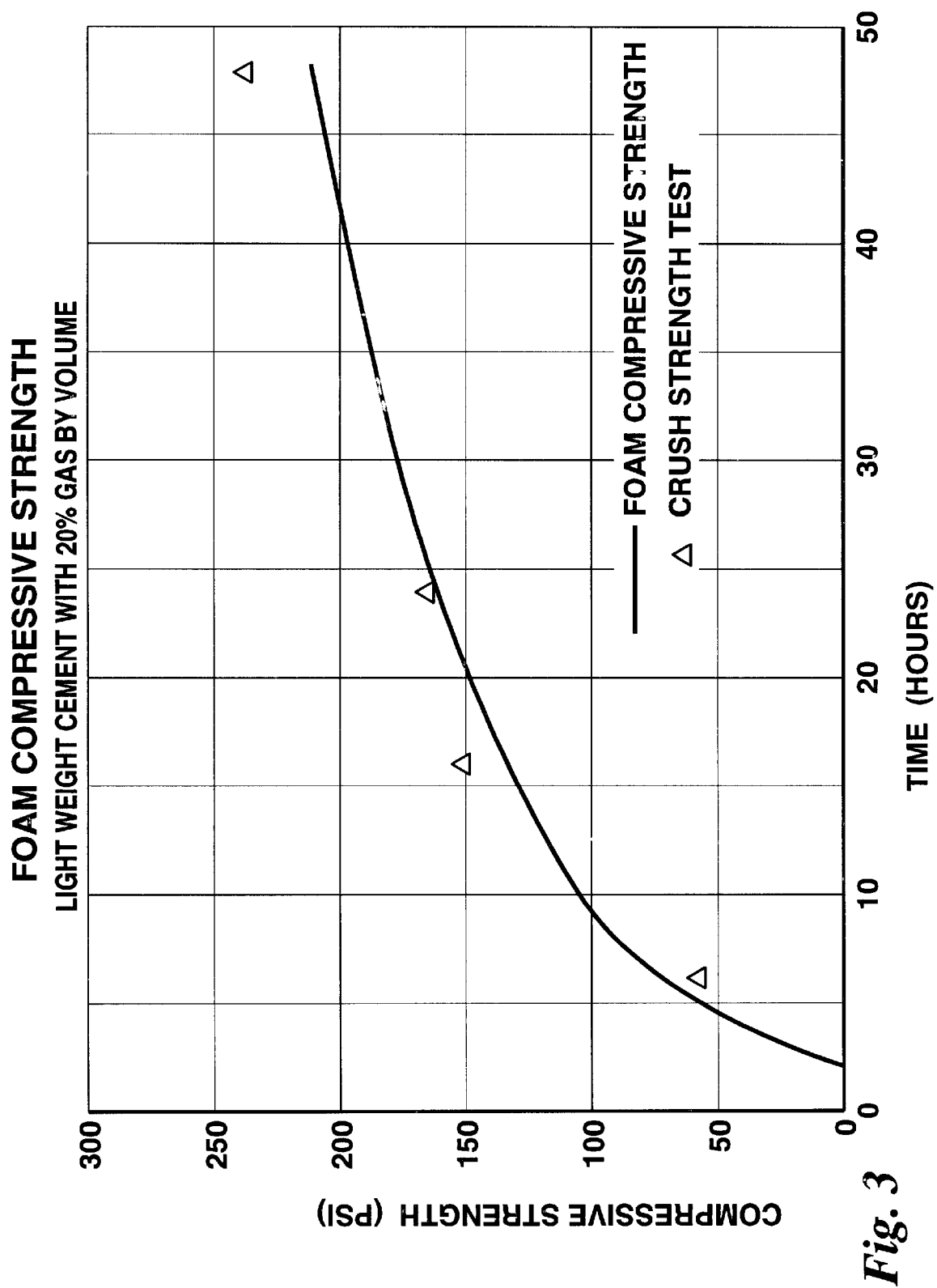
FIG. 3 shows a resulting compressive strength development of a foam cement over time when the surface of FIG. 2 is used in conjunction with data from a high temperature-high pressure cement analyzer.

The surface also may be expressed in a mathematical form which would be suitable for use by a control computer of a conventional high temperature-high pressure cement analyzer such as the UCA. If such a device is used to measure the base cement compressive strength, the foam cement compressive strength may be computed by the control computer over time as the cement sets so long as the volume percent entrained gas is known. The data may then be used to produce a graph or other display showing the compressive strength development over time of a desired foam cement. FIG. 3 shows the output of such a device used to provide the strength of a medium weight cement having 9% entrained gas by volume. Also shown on the graph are the crush strengths of cubes of the cement of interest. The crush test data verifies the accuracy of the process.

It should be understood that the accuracy of the prediction will be based at least somewhat on the number of data points used to generate the curves and surfaces hereinabove described. Moreover, while the generalized graphical relationship is of sufficient accuracy for use in oil field cementing applications, if more accurate results are desired, a calibration curve for a particular type of cement can be derived and substituted therefor. It also should be appreciated that it is well within the ability of one ordinarily skilled in the art to generate, without undue experimentation, the empirical data used to support the inventive method.

The inventive method may be implemented in a variety of ways. For example, the curves and surfaces used to predict the foam cement compressive strengths may be embodied in physical or computer generated graphical or numeric displays from which a user can determine the foam cement compressive strength of a cement of interest by locating the points representing base cement compressive strength and percent entrained gas by volume and reading the corresponding foam cement value. The method may alternatively be embodied in a computer program or routine wherein equations representing the curves and surfaces are used to calculate the foam cement value, which is subsequently displayed or recorded by a computer or other processor driven device.

In another aspect of the invention, the control computer or processor of a high temperature- high pressure cement analyzer is used to generate a display or recording of foam cement compressive strength based upon the measurement by the analyzer of the base cement compressive strength of a cement or cement slurry sample and an input of a selected volume percent of entrained gas. The computer or processor may access a look up table wherein numeric values representing the factors are stored for ranges of interest or use equations representing the generated curves and surfaces to determine or compute the corresponding value of the foam cement compressive strength based upon the predetermined relationship. In this manner, a time history may be obtained by computing the foam cement compressive strength as the cement sets. A preferred form of the invention can be carried out using the components of a modified cement analyzer system wherein a control computer, generally having a multichannel capability, is connected to one or more temperature and pressure controlled autoclaves. Also connected to the control computer is a digital plotter or other display device and a keyboard or other input means for entering data and command functions into the system. A sample placed in a pressure vessel in the autoclave is coupled to transducer means under computer control. Ultrasonic energy is propagated through the sample and the transit time is measured. A predetermined relationship relating transit time to compressive strength is employed and enables the determination of compressive strength of the base cement. The measurements may be repetitively performed on multiple samples simultaneously and the time history of the development of compressive strength of the base cement is obtained. Upon each determination of the compressive strength of the base cement, the compressive strength of a foam cement of interest having a given percent entrained gas by volume is determined according to the predetermined relationship relating base cement compressive strength and volume percent entrained gas to foam cement compressive strength. The control computer may then display or record the estimated compressive strength of the foam cement.

While the invention has been described with a certain degree of particularity, it is understood that the invention is not limited to the embodiment(s) set for herein for purposes of exemplification, but is to be limited only by the scope of the attached claim or claims, including the full range of equivalency to which each element thereof is entitled.

What is claimed is:

1. A method of estimating the compressive strength of a foam cement, comprising:
   (a) determining a compressive strength of a base cement of said foam cement;
   (b) determining a percent entrained gas by volume of said foam cement;
   (c) estimating the compressive strength of said foam cement using at least said determined compressive strength and said determined percent entrained gas by volume.

2. The method according to claim 1, further comprising:
   (d) displaying or recording the compressive strength of said foam cement.

3. An ultrasonic cement analyzer having a memory which contains data representing a predetermined relationship relating base cement compressive strength and percent entrained gas by volume to foam cement compressive strength, such that the compressive strength of a foam cement having a given percent entrained gas by volume, and having a base cement having a determined compressive strength, is determined in said ultrasonic cement analyzer according to the method of claim 1.

4. A method according to claim 1, wherein is provided a predetermined functional relationship relating at least base cement compressive strength and percent entrained gas by volume to foam cement compressive strength, and wherein step (c) includes the step of:
   (c1) determining, according to said predetermined relationship, said compressive strength of said foam cement using said determined compressive strength and said determined percent entrained gas.

5. The method according to claim 1, wherein step (a) is accomplished in a high temperature-high pressure cement analyzer.

6. The method according to claim 5, further comprising:
   (d) repetitively performing steps (a) and (c) over time as said base cement sample sets to obtain a time history of foam cement compressive strength.

7. The method according to claim 6, further comprising:
   (e) displaying or recording the compressive strength of said foam cement.

8. A method of estimating the compressive strength of a foam cement, comprising:
   (a) maintaining a base cement slurry sample at a controlled temperature and pressure;
   (b) transmitting an ultrasonic signal through said sample;
   (c) detecting said ultrasonic signal subsequent to its transiting said sample and measuring the time required for said signal to transit said sample;
   (d) determining, according to a predetermined relationship relating transit time to compressive strength, the compressive strength of said sample;
   (e) determining, according to a predetermined relationship relating base cement compressive strength and volume percent entrained gas to foam cement compressive strength, the compressive strength of a foam cement having a given entrained gas by volume;

(f) and displaying or recording the compressive strength of said foam cement.

9. A method of estimating the compressive strength of a foam cement, comprising:

(a) correlating the compressive strength of a base cement and a volume percent entrained gas to the compressive strength of said foam cement using empirically derived correlation data; and (b) determining from said compressive strength of said base cement and said volume percent entrained gas the compressive strength of said foam cement.

10. The method according to claim 9, wherein said correlation data comprise a graphical display or a numeric display.

11. The method according to claim 10, wherein said correlation data is empirically derived by:

measuring the crush strength of a plurality of foam cement samples, each of said samples having one or more volume percent entrained gas and having a base cement having a known compressive strength;

generating a set of curves representing said crush strength as a function of the compressive strength of said base cement; and generating a three-dimensional surface, said three-dimension surface having an X-axis, Y-axis, and Z-axis, with base cement compressive strength and percent entrained gas volume plotted along said X-axis and said Y-axis and foam cement compressive strength plotted along said Z-axis.

12. The method according to claim 10, wherein said correlation data are represented in a mathematical form.

13. The method according to claim 12, wherein said correlation data are fit by a function characterized by one or more constant coefficients.

* * * * *